(12) United States Patent
Aoyagi et al.

(10) Patent No.: US 7,760,358 B1
(45) Date of Patent: Jul. 20, 2010

(54) FILM MEASUREMENT

(75) Inventors: Paul Aoyagi, Sunnyvale, CA (US); Leonid Poslavsky, Belmont, CA (US)

(73) Assignee: KLA-Tencor Corporation, Milpitas, CA (US)

( * ) Notice: Subject to any disclaimer, the term of this patent is extended or adjusted under 35 U.S.C. 154(b) by 538 days.

(21) Appl. No.: 11/669,995

(22) Filed: Feb. 1, 2007

(51) Int. Cl.
*G01J 4/00* (2006.01)

(52) U.S. Cl. .................................. 356/369; 356/630

(58) Field of Classification Search ................. 356/369, 356/630, 625
See application file for complete search history.

(56) References Cited

U.S. PATENT DOCUMENTS

| | | | | |
|---|---|---|---|---|
| 7,190,453 | B1 * | 3/2007 | Aoyagi et al. ............... | 356/369 |
| 7,345,761 | B1 * | 3/2008 | Aoyagi et al. ............... | 356/369 |
| 7,362,686 | B1 * | 4/2008 | Aoyagi et al. ............... | 369/100 |
| 7,375,828 | B1 * | 5/2008 | Aoyagi et al. ............... | 356/625 |

OTHER PUBLICATIONS

Moharam et al., Formulation for Stable and Efficient Implementation of the Rigorous Coupled-Wave Analysis of Binary Gratings, J. Opt. Soc. Am., vol. 12, No. 5, pp. 1068-1076 (1995).

Li, Formulation and Comparison of Two Recursive Matrix Algorithms for Modeling Layered Diffraction Gratings, J. Opt. Soc. Am., vol. 13, No. 5, pp. 1024-1035 (1996).

* cited by examiner

*Primary Examiner*—L. G Lauchman
(74) *Attorney, Agent, or Firm*—Luedeka, Neely & Graham, P.C.

(57) ABSTRACT

The above and other needs are met by a method of determining actual properties of a film stack by directing an incident beam of light towards the film stack, such that the incident beam of light is reflected from the film stack as a reflected beam of light. The actual properties of the reflected beam of light are measured, and properties of the film stack are estimated. A mathematical model of the film stack is solved with the estimated properties of the film stack, to yield theoretical properties of the reflected beam of light. The mathematical model is solved in part using a fast Z-matrix algorithm. The theoretical properties of the reflected beam of light are compared to the actual properties of the reflected beam of light, to yield a cost function. The estimated properties of the film stack are iteratively adjusted, and the mathematical model is iteratively solved, until the cost function is within a desired tolerance. The estimated properties of the film stack are reported as the actual properties of the film stack.

20 Claims, 1 Drawing Sheet

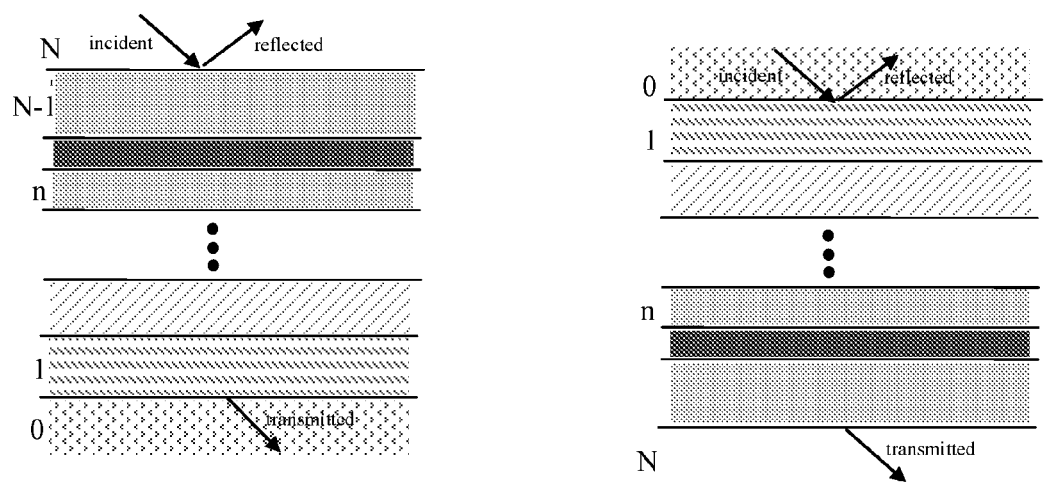

FILM MEASUREMENT

FIELD

This invention relates to the field of film measurement. More particularly, this invention relates to a system for improving the speed and accuracy of multi layered film stack thickness measurement and other property measurement, such as in the integrated circuit fabrication industry.

BACKGROUND

Integrated circuits are formed of many layers of different materials, which layers are patterned so as to form desired structures that interact with one another according to predetermined designs. Thus, it is of vital importance that many of these layers be formed to very exacting tolerances, such as in their shape, thickness, and composition. If the various structures so formed during the integrated circuit fabrication process are not precisely formed, then the integrated circuit tends to not function in the intended manner, and may not function at all.

As the term is used herein, "integrated circuit" includes devices such as those formed on monolithic semiconducting substrates, such as those formed of group IV materials like silicon or germanium, or group III-V compounds like gallium arsenide, or mixtures of such materials. The term includes all types of devices formed, such as memory and logic, and all designs of such devices, such as MOS and bipolar. The term also comprehends applications such as flat panel displays, solar cells, and charge coupled devices.

Because the layers of which integrated circuits are formed are so thin and patterned to be so small, they cannot be inspected without the aid of instrumentation. The precision of the instrumentation used is, therefore, vital to the successful production of integrated circuits. Thus, any improvement that can be made in the accuracy of such instrumentation is a boon to the integrated circuit fabrication industry. In addition, any improvement in the speed at which such instrumentation can take its readings is also of benefit to the industry, as such speed enhancements tend to reduce the production bottlenecks at inspection steps, or alternately allow for the inspection of a greater number of integrated circuits at such inspection steps.

Spectral ellipsometers and dual beam spectrophotometers are typically used to measure properties such as thickness and refractive index of individual layers within a multilayered film stack. Such instruments work by directing one or more beams of light toward the surface of the film stack, and then sensing the properties of the light as it is variously reflected off of the different surfaces of the individual layers within the film stack. By adjusting the properties of the incident beam of light, and detecting the associated changes in the reflected beam of light, the properties of the film stack, such as the materials of which the various layers are formed and the thicknesses to which they are formed, can be determined. Such methods typically involve solving Maxwell's equations, which provide a model for such systems.

This film measurement process can be broken down into two basic steps, being 1) the measurement of the properties of the reflected light beam, and 2) the mathematical fitting of reflectance property values from Maxwell's equations, which are solved or estimated, to the measured results attained in step 1. Step 2 typically consists of the iterated steps of computing one or more theoretical values by plugging estimates of the film stack parameters, such as thickness and refractive index, into the model film stack equations, comparing the theoretical values obtained to the actual measured property values of the reflected beam of light, and if the theoretical values and the measured values do not agree to within a desired tolerance, then adjusting the estimated film stack parameters and recomputing the theoretical values.

This process is performed again and again, each time making some adjustment to the estimated film stack parameters that are fed into the model, until the theoretical values computed by the model agree with the actual measured values within the desired precision limits. When this agreement is attained, then there is some confidence that the estimated film stack parameters that were used to produce the theoretical values are very nearly the same as the actual film stack parameters.

For film stacks containing non-isotropic, inhomogeneous layers, such as layers containing metal patterns or gratings, the theoretical values are commonly generated by mathematical models based on either the rigorous coupled wave analysis or modal method.

The reflectance equations that are derived for film stacks that generate multiple plane waves traveling at different angles are typically formulated using at least one of the S matrix algorithm or the R matrix algorithm, as understood by those with skill in the art. However, these algorithms are computationally burdensome, and require a longer than desirable period of time—and greater than desirable computational resources—to solve. Another well-known alternate formulation for computing the reflectance is the T matrix algorithm. Although this algorithm is more computationally efficient, it is highly susceptible to computational overflow error and is therefore seldom used in practical applications.

What is needed is a method to improve the efficiency of the electromagnetic field computation of multilayer structures containing patterned dielectric structures.

SUMMARY

The above and other needs are met by a method of determining actual properties of a film stack by directing an incident beam of light towards the film stack, such that the incident beam of light is reflected from the film stack as a reflected beam of light. The actual properties of the reflected beam of light are measured, and properties of the film stack are estimated. A mathematical model of the film stack is solved with the estimated properties of the film stack, to yield theoretical properties of the reflected beam of light. The mathematical model is solved in part using a fast Z-matrix algorithm. The theoretical properties of the reflected beam of light are compared to the actual properties of the reflected beam of light, to yield a cost function. The estimated properties of the film stack are iteratively adjusted, and the mathematical model is iteratively solved, until the cost function is within a desired tolerance. The estimated properties of the film stack are reported as the actual properties of the film stack.

BRIEF DESCRIPTION OF THE DRAWINGS

Further advantages of the invention are apparent by reference to the detailed description when considered in conjunction with the FIGURE, which is not to scale so as to more clearly show the details, wherein like reference numbers indicate like elements, and wherein is depicted a multi-layered film stack as both a non-inverted and an inverted film stack.

DETAILED DESCRIPTION

The purpose of this invention is to improve the efficiency of the spectral ellipsometer (SE) and the dual-beam spectrophotometer (DBS and polarized DBS) that measure thickness and material parameters of multilayered film stacks containing patterned metal and non-metal lines, with or without using precomputed libraries.

The various embodiments of this invention make it possible for a fast Z-Matrix method to compute the total electromagnetic fields in any arbitrary layer, while incurring negligible computational overhead. The embodiments of the invention improve the efficiency of computing the fields inside a film layer relative to the conventionally used S-Matrix method by about four times. This invention can be implemented as an add-in to existing instrument software.

The unique features of this invention include: 1) the definition of a novel field transmittance that allows us to efficiently compute the transmittance, and 2) the judicious ordering of matrix-vector multiplications that eliminate $O(N^3)$ overhead.

The embodiments of the present invention differ from conventional methods in that we have developed a more efficient method of computing the S-Matrix. Of note, we use a variant of the fast Z Matrix algorithm to compute the S-Matrix. By doing so, we realize two important advantages over the conventional S-Matrix computation algorithm. The first is that we can reduce the computational time by about 20-35%, when the number of layers is greater than four. The second—and possibly more significant—advantage is reduced code management and maintenance. That is, we can leverage existing software infrastructure based on the highly efficient fast Z-Matrix algorithm and, with minor modification, make the same code as computationally efficient as the S-Matrix for special film stack configurations and library generation. Details of the S-Matrix computation using a fast Z-Matrix algorithm are given below.

Two-Dimensional RCWA Formulation

Maxwell's equations (uniaxial media):

$$\nabla \times h = j\omega\epsilon_0 \bar{\bar{\epsilon}} e \qquad (1a)$$

$$\nabla \times e = -j\omega\mu_0 \bar{\bar{\mu}} h \qquad (1b)$$

where e=electric field, h=magnetic field, $$\bar{\bar{\epsilon}} = \begin{bmatrix} \epsilon & 0 & 0 \\ 0 & \epsilon & 0 \\ 0 & 0 & \epsilon_z \end{bmatrix}$$

=relative electric permittivity tensor, $$\bar{\bar{\mu}} = \begin{bmatrix} \mu & 0 & 0 \\ 0 & \mu & 0 \\ 0 & 0 & \mu_z \end{bmatrix}$$

=relative magnetic permeability tensor, $(\epsilon_0,\mu_0)$=electric permittivity and magnetic permeability of free space, respectively.

Assume the dielectric and magnetic permittivity has a periodic distribution in x and y directions of a Cartesian coordinate system. Mathematically, we can write $$A = \sum_{n=-N}^{N} \sum_{m=-M}^{M} a_{m,n} e^{-j\frac{2\pi m}{P_x}x} e^{-j\frac{2\pi n}{P_y}y} \qquad (2)$$

where A=Fourier transform representation of the distribution v, where:

$$v \in \left(\epsilon, \mu, \epsilon_z, \mu_z, \frac{1}{\epsilon}, \frac{1}{\mu}, \frac{1}{\epsilon_z}, \frac{1}{\mu_z}\right)$$

$P_x$, $P_y$=period in x, y directions, respectively, (M,N)=number of positive and negative modes in the x and y directions, respectively.

An incident plane wave solution to equations (1) is given by $$e_{inc}, h_{inc} \propto e^{\pm jk_0 k \cdot r} \qquad (3)$$

where $k = k_{x0}\hat{x} + k_{y0}\hat{y} + k_{z0}\hat{z}$=wave vector, $r = x\hat{x} + y\hat{y} + z\hat{z}$.

Phase matching at the boundary requires that the electric and magnetic fields are expressible as a superposition of Floquet harmonics, i.e., $$f = \sum_{n=-N}^{N} \sum_{m=-M}^{M} f_{m,n}(z) e^{j\left(\frac{2\pi m}{P_x} - k_{x0}\right)x} e^{j\left(\frac{2\pi n}{P_y} - k_{y0}\right)y} \quad \text{where} \qquad (4)$$

$$f \in \{e_x, e_y, e_z, h_x, h_y, h_z\}$$

For purposes of keeping track of the cross-modal interactions, it is convenient to remove the explicit dependence on the Fourier and Floquet harmonics and rewrite equations (3) and (4) as a matrix and (5) as a column vector, i.e., $$A = \begin{bmatrix} A'_0 & A'_{-1} & \dots & A'_{-2N} \\ A'_1 & A'_0 & \dots & A'_{-(2N-1)} \\ . & . & \dots & . \\ A'_{2N} & A'_{2N-1} & \dots & A'_0 \end{bmatrix}, \quad f = \begin{bmatrix} f_{-N} \\ f_{-(N-1)} \\ . \\ f_N \end{bmatrix} \qquad (5)$$

where the subscripts correspond to the Floquet harmonic numbers and the matrix elements of equation (5) are themselves matrices and vectors, i.e., $$A'_n = \begin{bmatrix} a_{0,n} & a_{-1,n} & \dots & a_{-2M,n} \\ a_{1,n} & a_{0,n} & \dots & a_{-(2M-1),n} \\ . & . & \dots & . \\ a_{2M,n} & a_{2M-1,n} & \dots & a_{0,n} \end{bmatrix}, \quad f_n = \begin{bmatrix} f_{-M,n} \\ f_{-(M-1),n} \\ . \\ f_{M,n} \end{bmatrix} \qquad (6)$$

We note that the ordering of the elements of equations (5) and (6) is arbitrary provided we maintain 1) the correspondence between the vector elements and the Floquet harmonics, and 2) the correspondence between the matrix elements and the Fourier harmonics. For one dimensional periodicity (e.g., x periodic, y constant) N=0, and equations (5) and (6) reduce to $A=A'_0$ and $f=f_0$.

Expanding equation (1) yields:

$$e_x = \left(\frac{1}{j\omega\varepsilon_0}\right) A_{1/\varepsilon} \left(\frac{\partial h_z}{\partial y} - \frac{\partial h_y}{\partial z}\right) \tag{6a}$$

$$e_y = \left(\frac{1}{j\omega\varepsilon_0}\right) A_{1/\varepsilon} \left(\frac{\partial h_x}{\partial z} - \frac{\partial h_z}{\partial x}\right) \tag{6b}$$

$$e_z = \left(\frac{1}{j\omega\varepsilon_0}\right) A_{1/\varepsilon} \left(\frac{\partial h_y}{\partial x} - \frac{\partial h_x}{\partial y}\right) \tag{6c}$$

$$h_x = \left(\frac{1}{j\omega\mu_o}\right) A_{1/\mu} \left(-\frac{\partial e_z}{\partial y} + \frac{\partial e_y}{\partial z}\right) \tag{6d}$$

$$h_y = \left(\frac{1}{j\omega\mu_o}\right) A_{1/\mu} \left(\frac{\partial e_x}{\partial z} + \frac{\partial e_z}{\partial x}\right) \tag{6e}$$

$$h_z = -\frac{1}{j\omega\mu_o} A_{1/\mu_z} \left(\frac{\partial e_y}{\partial x} - \frac{\partial e_x}{\partial y}\right) \tag{6f}$$

where the subscript of A denotes the permittivity and permeability distribution function being approximated by the Fourier transform. Substituting equation (6f) into equation (1) yields:

$$e_x - \frac{1}{k_o^2} A_{1/\varepsilon} \frac{\partial}{\partial y} A_{1/\mu_z} \left(\frac{\partial e_y}{\partial x} - \frac{\partial e_x}{\partial y}\right) = \frac{j\omega\mu_o}{k_o^2} A_{1/\varepsilon} \frac{\partial h_y}{\partial z} \tag{7}$$

Recalling the implicit dependence of e and h on the Floquet harmonics, i.e., equation (4), substituting derivatives with the appropriate diagonal matrices yields:

$$(I - A_{1/\varepsilon} K_y A_{1/\mu_z} K_y) e_x + A_{1/\varepsilon} K_y A_{1/\mu_z} K_x e_y = \frac{j\omega\mu_o}{k_o^2} A_{1/\varepsilon} \frac{\partial h_y}{\partial z} \tag{8}$$

Interchanging the x,y components and changing the sign to derive the x component yields:

$$-(I - A_{1/\varepsilon} K_x A_{1/\mu_z} K_x) e_y - A_{1/\varepsilon} K_x A_{1/\mu_z} K_y e_x = \frac{j\omega\mu_o}{k_o^2} A_{1/\varepsilon} \frac{\partial h_x}{\partial z} \tag{9}$$

Defining the tangential field vectors as:

$$e_t = \begin{bmatrix} e_x \\ e_y \end{bmatrix}, \quad h_t = \begin{bmatrix} h_x \\ h_y \end{bmatrix} \tag{10}$$

Therefore:

$$A_h'^{-1} e_t = \frac{j\omega\mu_o}{k_o^2} \frac{\partial h_t}{\partial z} \tag{11a}$$

where $$A_h'^{-1} = A_{1/\varepsilon}^{-1} \begin{bmatrix} -A_{1/\varepsilon} K_x A_{1/\mu_z} K_y & (-I + A_{1/\varepsilon} K_x A_{1/\mu_z} K_x) \\ (I - A_{1/\varepsilon} K_y A_{1/\mu_z} K_y) & A_{1/\varepsilon} K_y A_{1/\mu_z} K_x \end{bmatrix}. \tag{11b}$$

From E,H duality:

$$A_e'^{-1} h_t = -\frac{j\omega\varepsilon_o}{k_o^2} \frac{\partial e_t}{\partial z} \tag{12a}$$

where $$A_e'^{-1} = A_{1/\mu}^{-1} \begin{bmatrix} -A_{1/\mu} K_x A_{1/\varepsilon} K_y & (-I + A_{1/\mu} K_x A_{1/\varepsilon} K_x) \\ (I - A_{1/\mu} K_y A_{1/\varepsilon_z} K_y) & A_{1/\mu} K_y A_{1/\varepsilon_z} K_x \end{bmatrix}. \tag{12b}$$

Substituting equation (11) into equation (10) to form a differential equation yields:

$$S_h^2 h_t = A_h'^{-1} A_e'^{-1} h_t = -\frac{1}{k_o^2} \frac{\partial^2 h_t}{\partial z^2} \tag{13}$$

The general solutions to (13) include:

$$h_t = e^{jk_o S_h z} d_+ + e^{-jk_o S_h z} d_- \tag{14}$$

From (12a) we see that:

$$e_t = \frac{j\omega\mu_0}{k_o^2} A_h' jk_o S_h (e^{jk_o S_h z} d_+ - e^{-jk_o S_h z} d_-) = \tag{15}$$

$$-\frac{\omega\mu_0}{k_o} \eta_{h,n} (e^{jk_o S_h z} d_+ - e^{-jk_o S_h z} d_-)$$

where $\eta_h = A'_h S_h$=intrinsic impedance.

Using duality we can obtain a parallel set of equations in terms of $e_t$, i.e.:

$$S_e^2 e_t = A_e'^{-1} A_h'^{-1} e_t = -\frac{1}{k_o^2} \frac{\partial^2 e_t}{\partial z^2} \tag{16}$$

$$e_t = e^{jk_o S_e z} d_+ + e^{-jk_o S_e z} d_-$$

$$h_t = \frac{\omega\varepsilon_0}{k_o} \eta_{e,n} (e^{jk_o S_e z} d_+ - e^{-jk_o S_e z} d_-) \tag{17}$$

where $\eta_e = A'_e S_e$=intrinsic impedance.

By simplifying for non-magnetic media $A_{1/\mu} = A_{1/\mu_z} = I$, i.e.:

$$S_h^2 = A_{1/\varepsilon}^{-1} \begin{bmatrix} -A_{1/\varepsilon} K_x A_{1/\mu_z} K_y & (-I + A_{1/\varepsilon} K_x A_{1/\mu_z} K_x) \\ (I - A_{1/\varepsilon} K_y A_{1/\mu_z} K_y) & A_{1/\varepsilon} K_y A_{1/\mu_z} K_x \end{bmatrix} \tag{18}$$

$$\begin{bmatrix} -K_x A_{1/\varepsilon_z} K_y & (-I + K_x A_{1/\varepsilon_z} K_x) \\ (I - K_y A_{1/\varepsilon_z} K_y) & K_y A_{1/\varepsilon_z} K_x \end{bmatrix}$$

and expanding equation (16) produces:

$$S_h^2 = A_{1/\varepsilon}^{-1} \begin{bmatrix} A_{1/\varepsilon} K_x^2 K_y A_{1/\varepsilon_z} K_y + (-I + A_{1/\varepsilon} K_x^2)(I - K_y A_{1/\varepsilon_z} K_y) & -A_{1/\varepsilon} K_x K_y(-I + K_x A_{1/\varepsilon_z} K_x) + (-I + A_{1/\varepsilon} K_x^2) K_y A_{1/\varepsilon_z} K_x \\ -(I - A_{1/\varepsilon} K_y^2) K_x A_{1/\varepsilon_z} K_y + A_{1/\varepsilon} K_y K_x (I - K_y A_{1/\varepsilon_z} K_y) & (I - A_{1/\varepsilon} K_y^2)(-I + K_x A_{1/\varepsilon_z} K_x) + A_{1/\varepsilon} K_x K_y^2 A_{1/\varepsilon_z} K_x \end{bmatrix} \quad (19)$$

$$S_h^2 = A_{1/\varepsilon}^{-1} \begin{bmatrix} (-I + K_y A_{1/\varepsilon_z} K_y + A_{1/\varepsilon} K_x^2) & A_{1/\varepsilon} K_x K_y - K_y A_{1/\varepsilon_z} K_x \\ -K_x A_{1/\varepsilon_z} K_y + A_{1/\varepsilon} K_y K_x & (-I + A_{1/\varepsilon} K_y^2 + K_x A_{1/\varepsilon_z} K_x) \end{bmatrix} \quad (20)$$

A similar simplification can be found for $S_e^2$ using duality.

Fast Z-Matrix Algorithm

The goal is to derive an algorithm based on field impedance (admittance) to compute the reflectance, transmittance, and fields inside a multi-layered film stack.

Derivation 2.1 Recursive Impedance Computation
Starting from:

$$\begin{bmatrix} h_{t,n} \\ e'_{t,n} \end{bmatrix} = \begin{bmatrix} I & I \\ \eta_{h,n} & -\eta_{h,n} \end{bmatrix} \begin{bmatrix} e^{jk_o S_{h,n} z} & 0 \\ 0 & e^{-jk_o S_{h,n} z} \end{bmatrix} \begin{bmatrix} d_{+,n} \\ d_{-,n} \end{bmatrix} \quad (1)$$

where $$e'_{t,n} = \frac{k_o}{\omega \mu_0} e_{t,n}, \text{ and} \quad (2)$$

$$\begin{bmatrix} h_{t,n} \\ e'_{t,n} \end{bmatrix} = \begin{bmatrix} d_{+,n} + d_{-,n} \\ \eta_{h,n}(d_{+,n} - d_{-,n}) \end{bmatrix} = \begin{bmatrix} e^{jk_o S_{h,n} z} d_{+,n} + e^{-jk_o S_{h,n} z} d_{-,n} \\ \eta_{h,n}(e^{jk_o S_{h,n} z} d_{+,n} - e^{-jk_o S_{h,n} z} d_{-,n}) \end{bmatrix}, \quad (3)$$

find $d_{\pm,n}$ in terms of tangential fields at the bottom of the layer $z=0$, i.e., $h_{t,n-1}, e_{t,n-1}$. We have:

$$d_{+,n} + d_{-,n} = h_{t,n-1} \quad (4)$$

$$d_{+,n} - d_{-,n} = \eta_{h,n}^{-1} e'_{t,n-1} \quad (5)$$

Therefore:

$$\begin{bmatrix} d_{+,n} \\ d_{-,n} \end{bmatrix} = \frac{1}{2} \begin{bmatrix} I & -\eta_{h,n}^{-1} \\ I & \eta_{h,n}^{-1} \end{bmatrix} \begin{bmatrix} h_{t,n-1} \\ e'_{t,n-1} \end{bmatrix}. \quad (6)$$

Relate $n^{th}$ and $(n-1)^{th}$ layer fields, i.e.:

$$\begin{bmatrix} h_{t,n} \\ e'_{t,n} \end{bmatrix} = \frac{1}{2} \begin{bmatrix} I & I \\ \eta_{h,n} & -\eta_{h,n} \end{bmatrix} \begin{bmatrix} e^{jk_o S_{h,n} z} & 0 \\ 0 & e^{-jk_o S_{h,n} z} \end{bmatrix} \begin{bmatrix} I & \eta_{h,n}^{-1} \\ I & -\eta_{h,n}^{-1} \end{bmatrix} \begin{bmatrix} h_{t,n-1} \\ e'_{t,n-1} \end{bmatrix} \quad (7a)$$

Recall $\eta_{h,n} = A'_{h,n} S_{h,n}$, $$\begin{bmatrix} h_{t,n} \\ e'_{t,n} \end{bmatrix} = \frac{1}{2} \underbrace{\begin{bmatrix} W_n & 0 \\ 0 & A'_{h,n} W_n \end{bmatrix}}_{W_A} \underbrace{\begin{bmatrix} I & I \\ K_{z,n} & -K_{z,n} \end{bmatrix}}_{P} \quad (7b)$$

$$\underbrace{\begin{bmatrix} e^{jk_o K_{z,n} z} & 0 \\ 0 & e^{-jk_o K_{z,n} z} \end{bmatrix}}_{K_{ph}=\text{phasematrix}} \underbrace{\begin{bmatrix} I & K_{z,n}^{-1} \\ I & -K_{z,n}^{-1} \end{bmatrix}}_{P^{-1}} \underbrace{\begin{bmatrix} W_n^{-1} & 0 \\ 0 & W_n^{-1} A'^{-1}_{h,n} \end{bmatrix}}_{W_A^{-1}} \begin{bmatrix} h_{t,n-1} \\ e'_{t,n-1} \end{bmatrix}.$$

Define an impedance (admittance), i.e., $$\begin{bmatrix} h_t \\ e'_t \end{bmatrix} = \begin{bmatrix} Y e_t \\ e'_t \end{bmatrix}.$$

Therefore, we can relate $Y_n$ and $Y_{n-1}$, i.e.:

$$\begin{bmatrix} Y_{n-1} e'_{t,n} \\ e'_{t,n} \end{bmatrix} = \frac{1}{2} \begin{bmatrix} W_n & 0 \\ 0 & A'_{h,n} W_n \end{bmatrix} \quad (8a)$$

$$\begin{bmatrix} I & I \\ K_{z,n} & -K_{z,n} \end{bmatrix} \begin{bmatrix} e^{jk_o K_{z,n} z} & e^{jk_o K_{z,n} z} K_{z,n}^{-1} \\ e^{-jk_o K_{z,n} z} & -e^{-jk_o K_{z,n} z} K_{z,n}^{-1} \end{bmatrix} \begin{bmatrix} W_n^{-1} Y_{n-1} e_{t,n-1} \\ W_n^{-1} A'^{-1}_{h,n} e_{t,n-1} \end{bmatrix}$$

Multiplying out:

$$\begin{bmatrix} Y_n e'_{t,n} \\ e'_{t,n} \end{bmatrix} = \frac{1}{2} \begin{bmatrix} W_n & 0 \\ 0 & A'_{h,n} W_n \end{bmatrix} \begin{bmatrix} e^{jk_o K_{z,n} z} + e^{-jk_o K_{z,n} z} & (e^{jk_o K_{z,n} z} - e^{-jk_o K_{z,n} z}) K_{z,n}^{-1} \\ (e^{jk_o K_{z,n} z} - e^{-jk_o K_{z,n} z}) K_{z,n} & (e^{jk_o K_{z,n} z} + e^{-jk_o K_{z,n} z}) \end{bmatrix} \quad (8b)$$

$$\begin{bmatrix} W_n^{-1} Y_{n-1} e'_{t,n-1} \\ W_n^{-1} A'^{-1}_{h,n} e'_{t,n-1} \end{bmatrix}$$

$$\begin{bmatrix} Y_n e'_{t,n} \\ e'_{t,n} \end{bmatrix} = \quad (8c)$$

$$\frac{1}{2} \begin{bmatrix} W_n(e^{jk_o K_{z,n}z} + e^{-jk_o K_{z,n}z}) & W_n(e^{jk_o K_{z,n}z} - e^{-jk_o K_{z,n}z})K_{z,n}^{-1} \\ A'_{h,n} W_n(e^{jk_o K_{z,n}z} - e^{-jk_o K_{z,n}z})K_{z,n} & A'_n W_n(e^{jk_o K_{z,n}z} + e^{-jk_o K_{z,n}z}) \end{bmatrix} \begin{bmatrix} W_n^{-1} Y_{n-1} e'_{t,n-1} \\ W_n^{-1} A'^{-1}_{h,n} e'_{t,n-1} \end{bmatrix}$$

$$\begin{bmatrix} Y_n e'_{t,n} \\ e'_{t,n} \end{bmatrix} = \frac{1}{2} \quad (8d)$$

$$\begin{bmatrix} W[(e^{jk_o K_{z,n}z} + e^{-jk_o K_{z,n}z})W^{-1} Y_{n-1} + (e^{jk_o K_{z,n}z} - e^{-jk_o K_{z,n}z})K_{z,n}^{-1} W^{-1} A'^{-1}_{h,n}] e'_{t,n-1} \\ A'_{h,n} W[K_{z,n}(e^{jk_o K_z z} - e^{-jk_o K_z z})W^{-1} Y_{n-1} + (e^{jk_o K_{z,n}z} + e^{-jk_o K_{z,n}z})W^{-1} A'^{-1}_{h,n}] e'_{t,n-1} \end{bmatrix}$$

$$\begin{bmatrix} Y_n e'_{t,n} \\ e'_{t,n} \end{bmatrix} = \frac{1}{2} \begin{bmatrix} W[(e^{jk_o K_{z,n}z} + e^{-jk_o K_{z,n}z})D_{o,n} + (e^{jk_o K_{z,n}z} - e^{-jk_o K_{z,n}z})O_n^{-1}] e'_{t,n-1} \\ O_n[(e^{jk_o K_z z} - e^{-jk_o K_z z})D_{o,n} + (e^{jk_o K_{z,n}z} + e^{-jk_o K_{z,n}z})O_n^{-1}] e'_{t,n-1} \end{bmatrix} \quad (8e)$$

Solving for $Y_n$:

$$Y_n = W_n Y'_n O_n^{-1} \quad (9)$$

where $$Y'_n = [(e^{jk_o K_{z,n}z} + e^{-jk_o K_{z,n}z})D_{o,n-1} + \quad (10)$$

$$(e^{jk_o K_{z,n}z} - e^{jk_o K_{z,n}z})O_n^{-1}]$$

$$[(e^{jk_o K_{z,n}z} + e^{-jk_o K_{z,n}z})D_{o,n-1} + (e^{jk_o K_{z,n}z} + e^{-jk_o K_{z,n}z})O_n^{-1}]^{-1}.$$

Of practical note, equation (10) is, in general, catastrophically susceptible to round-off error related to the presence of large exponential values, i.e., $e^{jk_o K_{z,n}z}$. Specifically, the problem arises whenever the ratio of a large exponential relative to the magnitudes of the $Y'_n$ elements exceeds the floating point accuracy of the machine (this can be verified by going through an LU decomposition/back substitution for a 2×2 matrix). This problem, for example, prevents us from simply computing the inverse and performing a matrix multiplication. We can reduce this error to the limits of floating point precision by noting that for large exponentials, the solution $Y'_n$ is the identity matrix, i.e.:

$$\lim_{k_o K_{z,n}z \to \infty} Y'_n = e^{jk_o K_{z,n}z}[D_{o,n-1} + O_n^{-1}][D_{o,n-1} + O_n^{-1}]^{-1} e^{-jk_o K_{z,n}z} = I \quad (11)$$

Consequently, we can use equation (11) to solve for column vectors of $Y'_n$ corresponding to large exponentials, while solving for the remaining column vectors corresponding to the small exponentials, using the usual LU decomposition and back substitution.

Alternately, we can rewrite equation (9) as:

$$Y_n = W_n Y''_n \quad (12)$$

where:

$$Y''_n = Y'_n O_n = \quad (13)$$

$$[(e^{jk_o K_{z,n}z} + e^{-jk_o K_{z,n}z})D_{o,n-1} +$$

-continued $$(e^{jk_o K_{z,n}z} - e^{-jk_o K_{z,n}z})O_n^{-1}][(e^{jk_o K_z z} - e^{-jk_o K_z z})D_{o,n-1} +$$

$$(e^{jk_o K_{z,n}z} + e^{-jk_o K_{z,n}z})O_n^{-1}]^{-1}.$$

2.2 Computing Reflectance From Impedance

Defining reflectance as:

$$R_{t,n} : \begin{bmatrix} d_{+,n} \\ d_{-,n} \end{bmatrix} = \begin{bmatrix} d_{+,n} \\ R_{t,n} d_{+,n} \end{bmatrix} \quad (14)$$

Relate $Y_n$ to $R_{t,n}$ using equations (5), (8) and (13):

$$\begin{bmatrix} d_{+,n} \\ R_{t,n} d_{+,n} \end{bmatrix} = \frac{1}{2} \begin{bmatrix} e^{jk_o S_{h,n}z} & 0 \\ 0 & e^{-jk_o S_{h,n}z} \end{bmatrix} \begin{bmatrix} I & \eta_{h,n}^{-1} \\ I & -\eta_{h,n}^{-1} \end{bmatrix} \begin{bmatrix} Y_{n-1} e'_{t,n-1} \\ e'_{t,n-1} \end{bmatrix} \quad (15)$$

Because the n−1 layer is semi-infinite, $\eta_{h,n-1} = Y_{n-1}^{-1}$. Therefore:

$$\begin{bmatrix} d_{+,n} \\ R_{t,n} d_{+,n} \end{bmatrix} = \frac{1}{2} \begin{bmatrix} e^{jk_o S_{h,n}z}(Y_{n-1} + \eta_{h,n}^{-1}) e'_{t,n-1} \\ e^{-jk_o S_{h,n}z}(Y_{n-1} - \eta_{h,n}^{-1}) e'_{t,n-1} \end{bmatrix}. \quad (16)$$

Therefore, an equation for $R_{t,n}$ is given by:

$$R_{t,n} = e^{-jk_o S_{h,n}z}(Y_{n-1} - \eta_{h,n}^{-1})(Y_{n-1} + \eta_{h,n}^{-1})^{-1} e^{-jk_o S_{h,n}z} \quad (17)$$

2.3 Computing Transmittance From Impedance

Defining transmittance as:

$$T_{N,n_0} : T_{N,n_0} d_{+,N} = d_{+,n_0} \quad (18)$$

To compute $T_{N,n_0}$ we introduce a field transmittance:

$$C_{n,n-1} : e'_{t,n-1} = C_{n,n-1} e'_{t,n}. \quad (19)$$

Substituting equation (18) into equation (8e) yields:

$$\begin{bmatrix} Y_n e'_{t',n} \\ e'_{t',n} \end{bmatrix} = \frac{1}{2} \begin{bmatrix} w[(e^{jk_o K_{z,n} z} + e^{-jk_o K_{z,n} z})D_{o,n} + (e^{jk_o K_{z,n} z} - e^{-jk_o K_{z,n} z})O_n^{-1}]C_{n,n-1} e'_{t',n} \\ O_n[(e^{jk_o K_z z} - e^{-jk_o K_z z})D_{o,n} + (e^{jk_o K_{z,n} z} + e^{-jk_o K_{z,n} z})O_n^{-1}]C_{n,n-1} e'_{t',n} \end{bmatrix}. \quad (20)$$

From equation (20) we get:

$$C_{n,n-1} = 2[(e^{jk_o K_z z} - e^{-jk_o K_z z})D_{o,n} + (e^{jk_o K_{z,n} z} + e^{-jk_o K_{z,n} z})O_n^{-1}]O_n^{-1}. \quad (21)$$

Using the recursive nature of equation (19), we can compute the field transmission between layer N−1 and $n_0$, i.e.:

$$C_{N-1,n_0} = C_{N-2,n_0} C_{N-1,N-2}. \quad (22)$$

To compute the transmittance $T_{N,n_0}$ from the field transmittance $C_{n,n_0}$, we need to define two conversion matrices $C_{N,N-1}$ and $C_{n_0,n_0-1}$ at the top (n=N) and bottom (n=$n_0$) layers that convert fields into propagating waves and vice-versa, i.e.:

$$e'_{t,N-1} = C_{N,N-1} d_{+,N}, \quad (23a)$$

$$d_{+,n_0} = C_{n_0,n_0-1} e'_{t,n_0}. \quad (23b)$$

Deriving $C_{N,N-1}$ and substituting equation (23a) into equation (16) yields:

$$\begin{bmatrix} d_{+,n} \\ R_{t,n} d_{+,N} \end{bmatrix} = \frac{1}{2} \begin{bmatrix} e^{jk_o S_{h,n} z}(Y_{n-1} + \eta_{h,n}^{-1}) e'_{t,n-1} \\ e^{-jk_o S_{h,n} z}(Y_{n-1} - \eta_{h,n}^{-1}) e'_{t,n-1} \end{bmatrix} = \quad (24)$$

$$\frac{1}{2} \begin{bmatrix} e^{jk_o S_{h,N} z}(Y_{n-1} + \eta_{h,N}^{-1}) C_{N,N-1} d_{+,N} \\ e^{-jk_o S_{h,N} z}(Y_{n-1} - \eta_{h,N}^{-1}) C_{N,N-1} d_{+,N} \end{bmatrix}$$

Therefore, $$2 = e^{jk_0 S_{h,N} z}(Y_{N-1} + \eta_{h,N}^{-1}) C_{N,N-1}, \quad (25)$$

$$C_{N,N-1} = 2(Y_{N-1} + \eta_{h,N}^{-1})^{-1} e^{-jk_0 S_{h,N} z}. \quad (26)$$

Derive $C_{n_0,n_0-1}$. In this case, the bottom layer is semi-infinite, $Y_{n_0-1} = \eta_{h,n_0}^{-1}$ or equivalently $R_{t,n_0-1} = 0$. At this point, we could also assume that z=0, however, we will retain this term to accommodate for possible reference plane shifting (virtual interface) associated with the sector S-matrix. Therefore:

$$\begin{bmatrix} C_{n_0,n_0-1} e'_{t,n_0} \\ 0 \end{bmatrix} = \quad (27a)$$

$$\frac{1}{2} \begin{bmatrix} e^{jk_o S_{h,n_0} z}(\eta_{h,n_0}^{-1} + \eta_{h,n_0}^{-1}) e'_{t,n_0} \\ e^{-jk_o S_{h,n_0-1} 0}(\eta_{h,n_0}^{-1} - \eta_{h,n_0}^{-1}) e'_{t,n_0} \end{bmatrix} = \begin{bmatrix} e^{jk_o S_{h,n_0} z} \eta_{h,n_0}^{-1} e'_{t,n_0} \\ 0 \end{bmatrix},$$

$$e^{-jk_o S_{h,n_0} z} \eta_{h,n_0}^{-1} = C_{n_0,n_0-1}. \quad (27b)$$

Summarizing, the transmittance between the top layer (N) to the bottom layer ($n_0$) is given by the product $$T_{N,n_0} = \prod_{n=n_0}^{N} C_{n,n-1}, \quad (28)$$

where:

$$C_{n,n-1} = \begin{cases} e^{-jk_o S_{h,n} z} \eta_{h,n}^{-1} & \text{for } n = \text{bottom layer index } (n_o) \\ 2(Y_{n-1} + \eta_{h,n}^{-1})^{-1} e^{-jk_o S_{h,n} z} & \text{for } n = \text{top layer index } (N) \\ 2[(e^{jk_o K_{z,n} z} - e^{-jk_o K_{z,n} z})D_{o,n} + (e^{jk_o K_{z,n} z} + e^{-jk_o K_{z,n} z})O_n^{-1}]^{-1} O_n^{-1} & \text{for } n_o < n < N \end{cases} \quad (29)$$

2.4 Efficient Computation Of Total Field At Any Layer

This computation boils down to computing $d_{\pm,m}$. Denote the layer in which we want to compute the field as m. First consider the case when m≠$n_0$, m≠N. From equations (1) and (18) of this section, the fields at the bottom of layer m (z=0) can be expressed as:

$$\begin{bmatrix} Y_m T_{N,m} d_{+,N} \\ \eta_{h,m}^{-1} T_{N,m} d_{+,N} \end{bmatrix} = \begin{bmatrix} d_{+,m} + d_{-,m} \\ (d_{+,m} + d_{-,m}) \end{bmatrix}. \quad (30)$$

Solving for $d_{\pm,m}$ in terms of a known incident propagating wave $d_{+,N}$ yields:

$$\frac{1}{2}(Y_m + \eta_{h,m}^{-1}) T_{N,m} d_{+,N} = d_{+,m}, \quad (31a)$$

$$\frac{1}{2}(Y_m - \eta_{h,m}^{-1}) T_{N,m} d_{+,N} = d_{-,m}. \quad (31b)$$

Substituting equations (31a) and (31b) into equation (1), we obtain a general expression for the fields inside the $m^{th}$ layer in terms of known quantities, i.e.:

$$\begin{bmatrix} h_{t,m} \\ e'_{t,m} \end{bmatrix} = \qquad (32)$$

$$\begin{bmatrix} \frac{1}{2}[e^{jk_o S_{h,m}z}(Y_m + \eta_{h,m}^{-1}) + e^{-jk_o S_{h,m}z}(Y_m - \eta_{h,m}^{-1})]T_{N,m}d_{+,N} \\ \frac{1}{2}\eta_{h,m}[e^{jk_o S_{h,m}z}(Y_m + \eta_{h,m}^{-1}) - e^{-jk_o S_{h,m}z}(Y_m - \eta_{h,m}^{-1})]T_{N,m}d_{+,N} \end{bmatrix}.$$

Consider the case when $m=n_0$ (the bottom layer). Equation (28) becomes precisely equal to the propagating wave transmission coefficient. Consequently:

$$T_{N,m}d_{+,N}=d_{+,n_0}. \qquad (33)$$

When m=N (the top layer), the field solution is trivial since $d_{+,N}$ is given by the known incident propagating wave, while $d_{-,N}$ can be computed directly from the multimodal reflectance $R_{t,N}$, i.e.:

$$d_{-,N}=R_{t,N}d_{+,N}. \qquad (34)$$

At first glance, equations (5), (6), (7), and (2b) appear to suggest that a field computation will increase the computational overhead of the fast Z-Matrix by requiring additional full matrix operations. We can, however, eliminate this overhead by performing the matrix-vector multiplication first, i.e., begin multiplication from $d_{+,N}$ and proceed from right to left. Moreover, we can store the product of equation (28), and this reduces the operation count of using equation (5) from $O(N^3)$ to $O(N^2)$.

Fast Z-Matrix Algorithm

The goal is to present an algorithm, based on the fast Z-matrix algorithm, to compute the S-Matrix of an arbitrary multi-layered film stack.

FIG. 1 depicts the decomposition of the S-Matrix computation of a multi-layered film stack into a non-inverted and an inverted film stack. Compare the computational efficiency of the new algorithm with the conventional algorithm Algorithm Step 1: Decompose the original film stack into two film stacks, namely, a non-inverted and inverted film stack, as depicted in FIG. 1.

Step 2: Compute the reflectance and transmittance at the top of both film stacks using the fast Z-matrix algorithm.

Step 3: By definition, the S-matrix S of the original film stack is given by:

$$S = \begin{bmatrix} T'_{0,N} & R_{t,N} \\ R'_{t,0} & T_{N,0} \end{bmatrix},$$

]where: $R_{t,N}$, $T_{N,0}$=the reflectance and transmittance of the non-inverted film stack, and $R'_{t,0}$, $T'_{0,N}$=the reflectance and transmittance of the inverted film stack, where the prime denotes the inverted stack.

Operation Count and Improved Efficiency

Fast Z-Matrix

We can derive a formula for the total major operation count of the fast Z-matrix algorithm as applied to the S-matrix computation, by noting that any given N-layered film stack will have one top layer, one bottom layer, and N-2 middle layers. Therefore, the total operation count=$M_z$=$M_{bot}$+$M_{top}$+(N-2)*$M_{mid}$, where $M_{bot}$, $M_{top}$, $M_{mid}$ are the major operation counts for the computation at the top, middle and bottom layers.

Conventional Algorithm

A formula for the total operation count can be derived by noting that for any given N-layered film stack we must build the full S-matrix by propagating sector S-matrices. Since each sector S-matrix characterizes a two-layer media, it is easy to show that there are (N-1) sector S-matrices and (N-2) S-matrix propagations to combine the sector S-matrices. Therefore, the total operation count $M_{standard}$=$M_{bot}$+(N-1)*$M_{sec}$+(N-2)*$M_{prop}$, where $M_{bot}$, $M_{sec}$, $M_{prop}$ are the major operation counts for the computation at the bottom, each sector and for the propagation.

Conclusion

The Z-matrix algorithm is more computationally efficient than the conventional algorithm for computing the S-matrix of a film stack with more than two layers. The improved efficiency of the Z-matrix algorithm is proportional to the number of layers. In the worst case, the improvement saturates to about 22%. In a more typical case the improvement saturates to about 32%. The improvement saturates (approximately) when the number of layers exceeds about ten. For a two-layer films stack, i.e., a sector S-matrix film stack, the Z-matrix algorithm has the same efficiency as the conventional algorithm.

The foregoing description of preferred embodiments for this invention has been presented for purposes of illustration and description. It is not intended to be exhaustive or to limit the invention to the precise form disclosed. Obvious modifications or variations are possible in light of the above teachings. The embodiments are chosen and described in an effort to provide the best illustrations of the principles of the invention and its practical application, and to thereby enable one of ordinary skill in the art to utilize the invention in various embodiments and with various modifications as are suited to the particular use contemplated. All such modifications and variations are within the scope of the invention as determined by the appended claims when interpreted in accordance with the breadth to which they are fairly, legally, and equitably entitled.

What is claimed is:

1. A processor-based method of determining actual properties of a film stack, the method comprising the steps of:
    directing an incident beam of light towards the film stack, such that the incident beam of light is reflected from the film stack as a reflected beam of light,
    measuring actual properties of the reflected beam of light,
    estimating properties of the film stack,
    solving a mathematical model of the film stack with the estimated properties of the film stack to yield theoretical properties of the reflected beam of light, using the processor, where the mathematical model is solved in part using a fast Z-matrix algorithm,
    comparing the theoretical properties of the reflected beam of light to the actual properties of the reflected beam of light to yield a cost function,
    iteratively adjusting the estimated properties of the film stack and solving the mathematical model until the cost function is within a desired tolerance, and
    reporting the estimated properties of the film stack as the actual properties of the film stack.

2. The method of claim 1, wherein the method is implemented in one of an ellipsometer and a reflectometer.

3. The method of claim 1, wherein the film stack comprises layers of more than one material.

4. The method of claim 1, wherein the film stack comprises more than one layer.

5. The method of claim 1, wherein the film stack includes a patterned layer.

6. The method of claim 1, wherein the actual properties of the film stack include at least one of layer thickness, refractive index, roughness, pattern geometry, material properties, offset between pattern layers, substrate properties, and tool model parameters.

7. The method of claim 1, wherein the mathematical model is a reflectance model that is derived using rigorous coupled wave analysis.

8. A processor-based method of determining actual properties of layered media, the method comprising the steps of:
   directing an incident beam of light towards the layered media, such that the incident beam of light is reflected from the layered media as a reflected beam of light,
   measuring actual properties of the reflected beam of light,
   estimating properties of the layered media,
   solving a mathematical model of the layered media with the estimated properties of the layered media to yield theoretical properties of the reflected beam of light, using the processor, where the mathematical model is solved in part using a fast Z-matrix algorithm,
   comparing the theoretical properties of the reflected beam of light to the actual properties of the reflected beam of light to yield a cost function,
   iteratively adjusting the estimated properties of the layered media and solving the mathematical model until the cost function is within a desired tolerance, and
   reporting the estimated properties of the layered media as the actual properties of the layered media.

9. The method of claim 8, wherein the method is implemented in an ellipsometer.

10. The method of claim 8, wherein the layered media comprises layers of more than one material.

11. The method of claim 8, wherein the layered media comprises more than one layer.

12. The method of claim 8, wherein the layered media includes a grating layer.

13. The method of claim 8, wherein the actual properties of the layered media include at least one of layer thickness and layer refractive index.

14. The method of claim 8, wherein the mathematical model is a reflectance model that is derived using rigorous coupled wave analysis.

15. The method of claim 8, wherein the method is implemented in a scatterometer.

16. The method of claim 8, wherein the layered media comprises a film stack on a semiconducting substrate.

17. The method of claim 8, wherein the fast Z-matrix is used in combination with an S matrix algorithm.

18. The method of claim 8, wherein the fast Z matrix algorithm is characterized by:

$$(I - A_{1/\varepsilon}K_y A_{1/\mu_z}K_y)e_x + A_{1/\varepsilon}K_y A_{1/\mu_z}K_x e_y = \frac{j\omega\mu_o}{k_o^2}A_{1/\varepsilon}\frac{\partial h_y}{\partial z},$$

$$-(I - A_{1/\varepsilon}K_x A_{1/\mu_z}K_x)e_y - A_{1/\varepsilon}K_x A_{1/\mu_z}K_y e_x = \frac{j\omega\mu_o}{k_o^2}A_{1/\varepsilon}\frac{\partial h_x}{\partial z}, \text{ and}$$

$$e_t = \begin{bmatrix} e_x \\ e_y \end{bmatrix}, \quad h_t = \begin{bmatrix} h_x \\ h_y \end{bmatrix},$$

where A and K are matrices of properties, $e_t$ and $h_t$ are tangential vector fields, and other terms have definitions as provided by Maxwell's equations.

19. The method of claim 1, wherein the fast Z matrix algorithm is characterized by:

$$(I - A_{1/\varepsilon}K_y A_{1/\mu_z}K_y)e_x + A_{1/\varepsilon}K_y A_{1/\mu_z}K_x e_y = \frac{j\omega\mu_o}{k_o^2}A_{1/\varepsilon}\frac{\partial h_y}{\partial z},$$

$$-(I - A_{1/\varepsilon}K_x A_{1/\mu_z}K_x)e_y - A_{1/\varepsilon}K_x A_{1/\mu_z}K_y e_x =$$

$$\frac{j\omega\mu_o}{k_o^2}A_{1/\varepsilon}\frac{\partial h_x}{\partial z}, \text{ and } e_t = \begin{bmatrix} e_x \\ e_y \end{bmatrix}, \quad h_t = \begin{bmatrix} h_x \\ h_y \end{bmatrix},$$

where A and K are matrices of properties, $e_t$ and $h_t$ are tangential vector fields, and other terms have definitions as provided by Maxwell's equations.

20. A processor-based method of determining a reflectance of a layered media by iteratively solving a mathematical model of the layered media with estimated properties of the layered media, where the mathematical model is solved with a processor using a fast Z matrix algorithm.

* * * * *